United States Patent
Biyani

(10) Patent No.: US 8,152,852 B2
(45) Date of Patent: Apr. 10, 2012

(54) VARIABLE HEIGHT VERTEBRAL BODY REPLACEMENT IMPLANT

(75) Inventor: Ashok Biyani, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 549 days.

(21) Appl. No.: 12/317,206

(22) Filed: Dec. 19, 2008

(65) Prior Publication Data

US 2009/0138083 A1     May 28, 2009

Related U.S. Application Data

(63) Continuation of application No. PCT/US2007/019921, filed on Sep. 13, 2007.

(60) Provisional application No. 60/844,887, filed on Sep. 14, 2006.

(51) Int. Cl.
*A61F 2/44* (2006.01)

(52) U.S. Cl. .................................................. 623/17.16

(58) Field of Classification Search .... 623/17.11–17.16; 606/60, 246–249
See application file for complete search history.

(56) References Cited

U.S. PATENT DOCUMENTS

| | | | | |
|---|---|---|---|---|
| 5,236,460 A * | 8/1993 | Barber | .................. | 623/17.15 |
| 5,290,312 A * | 3/1994 | Kojimoto et al. | .......... | 623/17.15 |
| 5,702,455 A * | 12/1997 | Saggar | .................. | 623/17.15 |
| 5,776,197 A * | 7/1998 | Rabbe et al. | .................. | 623/17.15 |
| 5,776,198 A * | 7/1998 | Rabbe et al. | .................. | 623/17.15 |
| 5,865,848 A * | 2/1999 | Baker | ........................ | 623/17.15 |
| 5,989,291 A * | 11/1999 | Ralph et al. | ................. | 623/17.15 |
| 6,063,121 A * | 5/2000 | Xavier et al. | ................. | 623/17.15 |
| 6,106,557 A * | 8/2000 | Robioneck et al. | ........ | 623/17.15 |
| 6,126,689 A * | 10/2000 | Brett | ........................ | 623/17.16 |
| 6,176,881 B1 * | 1/2001 | Schar et al. | ................. | 623/17.11 |
| 6,176,882 B1 * | 1/2001 | Biedermann et al. | ...... | 623/17.15 |
| 6,190,413 B1 * | 2/2001 | Sutcliffe | .................... | 623/17.11 |
| 6,190,414 B1 * | 2/2001 | Young et al. | ................. | 623/17.15 |
| 6,193,756 B1 * | 2/2001 | Studer et al. | ................ | 623/17.15 |
| 6,214,050 B1 * | 4/2001 | Huene | ........................ | 623/17.15 |
| 6,375,683 B1 * | 4/2002 | Crozet et al. | ................ | 623/17.15 |
| 6,395,034 B1 * | 5/2002 | Suddaby | .................... | 623/17.15 |
| 6,419,705 B1 * | 7/2002 | Erickson | .................... | 623/17.16 |
| 6,436,140 B1 * | 8/2002 | Liu et al. | .................... | 623/17.11 |
| 6,436,142 B1 * | 8/2002 | Paes et al. | .................. | 623/17.15 |
| 6,454,806 B1 * | 9/2002 | Cohen et al. | ................ | 623/17.15 |
| 6,454,807 B1 * | 9/2002 | Jackson | ...................... | 623/17.15 |
| 6,524,341 B2 * | 2/2003 | Lang et al. | ................. | 623/17.15 |
| 6,562,074 B2 * | 5/2003 | Gerbec et al. | .............. | 623/17.15 |
| 6,616,695 B1 * | 9/2003 | Crozet et al. | .............. | 623/17.11 |
| 6,641,614 B1 * | 11/2003 | Wagner et al. | ............ | 623/17.15 |
| 6,648,917 B2 * | 11/2003 | Gerbec et al. | .............. | 623/17.11 |
| 6,660,038 B2 * | 12/2003 | Boyer et al. | ............... | 623/17.15 |
| 6,730,088 B2 * | 5/2004 | Yeh | ............................... | 606/247 |
| 6,752,832 B2 * | 6/2004 | Neumann | .................. | 623/17.15 |
| 6,764,515 B2 * | 7/2004 | Ralph et al. | ................. | 623/17.13 |
| 6,805,714 B2 * | 10/2004 | Sutcliffe | .................... | 623/17.11 |
| 6,821,298 B1 * | 11/2004 | Jackson | ..................... | 623/17.15 |
| 6,830,589 B2 * | 12/2004 | Erickson | .................... | 623/17.15 |
| 6,852,129 B2 * | 2/2005 | Gerbec et al. | .............. | 623/17.15 |
| 6,863,673 B2 * | 3/2005 | Gerbec et al. | .................. | 606/99 |
| 6,866,682 B1 * | 3/2005 | An et al. | ..................... | 623/17.15 |

(Continued)

*Primary Examiner* — Alvin J Stewart
(74) *Attorney, Agent, or Firm* — Emch, Schaffer, Schaub & Porcello Co., L.P.A.

(57) ABSTRACT

A variable height vertebral body replacement implant used in corpectomy surgery to provide support in place of a removed or damaged vertebrae, and contain and compact bone graft material.

24 Claims, 11 Drawing Sheets

U.S. PATENT DOCUMENTS

| | | | | |
|---|---|---|---|---|
| 6,893,464 | B2* | 5/2005 | Kiester | 623/17.11 |
| 6,902,579 | B2* | 6/2005 | Harms et al. | 623/17.11 |
| 6,960,232 | B2* | 11/2005 | Lyons et al. | 623/17.16 |
| 7,014,659 | B2* | 3/2006 | Boyer et al. | 623/17.15 |
| 7,018,415 | B1* | 3/2006 | McKay | 623/17.15 |
| 7,311,733 | B2* | 12/2007 | Metz-Stavenhagen | 623/17.15 |
| 7,544,208 | B1* | 6/2009 | Mueller et al. | 623/17.15 |
| 7,575,601 | B2* | 8/2009 | Dickson | 623/17.15 |
| 7,641,693 | B2* | 1/2010 | Gutlin et al. | 623/17.15 |
| 7,645,295 | B2* | 1/2010 | Osman | 606/281 |
| 7,648,529 | B2* | 1/2010 | An et al. | 623/17.15 |
| 7,674,294 | B2* | 3/2010 | Karahalios et al. | 623/17.11 |
| 7,674,296 | B2* | 3/2010 | Rhoda et al. | 623/17.15 |
| 7,708,779 | B2* | 5/2010 | Edie et al. | 623/17.15 |
| 7,753,958 | B2* | 7/2010 | Gordon et al. | 623/17.15 |
| 7,763,076 | B2* | 7/2010 | Navarro et al. | 623/17.15 |
| 7,794,501 | B2* | 9/2010 | Edie et al. | 623/17.12 |
| 7,819,920 | B2* | 10/2010 | Assaker | 623/17.11 |
| 7,819,922 | B2* | 10/2010 | Sweeney | 623/17.16 |
| 7,828,846 | B2* | 11/2010 | Biedermann et al. | 623/17.13 |
| 7,867,279 | B2* | 1/2011 | Hester et al. | 623/17.14 |
| 7,871,441 | B2* | 1/2011 | Eckman | 623/17.11 |
| 7,879,096 | B2* | 2/2011 | Dickson et al. | 623/17.11 |
| 7,883,543 | B2* | 2/2011 | Sweeney | 623/17.15 |
| 7,887,596 | B2* | 2/2011 | Douget et al. | 623/17.16 |
| 7,909,870 | B2* | 3/2011 | Kraus | 623/17.15 |
| 7,914,581 | B2* | 3/2011 | Dickson et al. | 623/17.16 |
| 2002/0082696 | A1* | 6/2002 | Harms et al. | 623/17.11 |
| 2003/0014111 | A1* | 1/2003 | Ralph et al. | 623/17.13 |
| 2003/0045877 | A1* | 3/2003 | Yeh | 606/61 |
| 2003/0130739 | A1* | 7/2003 | Gerbec et al. | 623/17.15 |
| 2004/0044411 | A1* | 3/2004 | Suddaby | 623/17.15 |
| 2004/0049271 | A1* | 3/2004 | Biedermann et al. | 623/17.11 |
| 2004/0153160 | A1* | 8/2004 | Carrasco | 623/17.15 |
| 2005/0043800 | A1* | 2/2005 | Paul et al. | 623/17.15 |
| 2005/0060036 | A1* | 3/2005 | Schultz et al. | 623/17.15 |
| 2005/0085910 | A1* | 4/2005 | Sweeney | 623/17.11 |
| 2005/0113921 | A1* | 5/2005 | An et al. | 623/17.11 |
| 2005/0187634 | A1* | 8/2005 | Berry | 623/17.15 |
| 2006/0058877 | A1* | 3/2006 | Gutlin et al. | 623/17.11 |
| 2006/0069442 | A1* | 3/2006 | Michelson | 623/17.15 |
| 2006/0074490 | A1* | 4/2006 | Sweeney | 623/17.15 |
| 2006/0100710 | A1* | 5/2006 | Gutlin et al. | 623/17.15 |
| 2007/0191954 | A1* | 8/2007 | Hansell et al. | 623/17.15 |
| 2007/0255407 | A1* | 11/2007 | Castleman et al. | 623/17.11 |
| 2007/0270968 | A1* | 11/2007 | Baynham et al. | 623/17.11 |
| 2008/0004705 | A1* | 1/2008 | Rogeau et al. | 623/17.16 |
| 2008/0167718 | A1* | 7/2008 | Protopsaltis | 623/17.16 |
| 2008/0300598 | A1* | 12/2008 | Barreiro et al. | 606/63 |
| 2008/0306594 | A1* | 12/2008 | Zubok et al. | 623/17.15 |
| 2009/0005874 | A1* | 1/2009 | Fleischmann et al. | 623/17.16 |
| 2009/0112325 | A1* | 4/2009 | Refai et al. | 623/17.16 |
| 2009/0210061 | A1* | 8/2009 | Sledge | 623/17.15 |
| 2010/0010633 | A1* | 1/2010 | Kohm | 623/17.16 |
| 2010/0016971 | A1* | 1/2010 | Berry | 623/17.15 |
| 2010/0082109 | A1* | 4/2010 | Greenhalgh et al. | 623/17.15 |
| 2010/0191334 | A1* | 7/2010 | Keller | 623/17.15 |
| 2010/0211176 | A1* | 8/2010 | Greenhalgh | 623/17.15 |

* cited by examiner

VARIABLE HEIGHT VERTEBRAL BODY REPLACEMENT IMPLANT

CROSS REFERENCE TO RELATED APPLICATIONS

This application is a continuation-in-part of International Application No. PCT/US 2007/019921 filed 13, Sep. 2007, which is based upon and claims the benefit of U.S. provisional application No. 60/844,887 filed Sep. 14, 2006.

BACKGROUND OF THE INVENTION

This invention relates to the field of orthopedic surgery and more particularly to the area of spinal surgery. The present invention is a variable height vertebral body replacement implant and is designed to reconstruct the spinal column after part or all of a vertebral body has been removed. It consists of an open design, which is initially distracted and placed in the vertebral defect. Bone graft material is then placed in the cage like enclosure. Bone graft can be compacted within the cage as its open portion is completed.

SUMMARY OF THE INVENTION

The present invention is a variable height vertebral body replacement implant consisting of a top and bottom ring joined by telescoping rods. The variable length telescoping rods include a ratcheting mechanism for allowing the cage to be secured and released once implanted. Between the rings is a expandable mesh material that forms a three sided tubular cage. The mesh material has an opening on one side that allows for complete packing of the cage with bone graft material. After the bone graft is packed into the cage, a fourth lateral mesh wall is attached to the open side of the cage to form a completely contained cage structure.

DETAILED DESCRIPTION OF THE PREFERRED EMBODIMENT(S)

Figure 1:
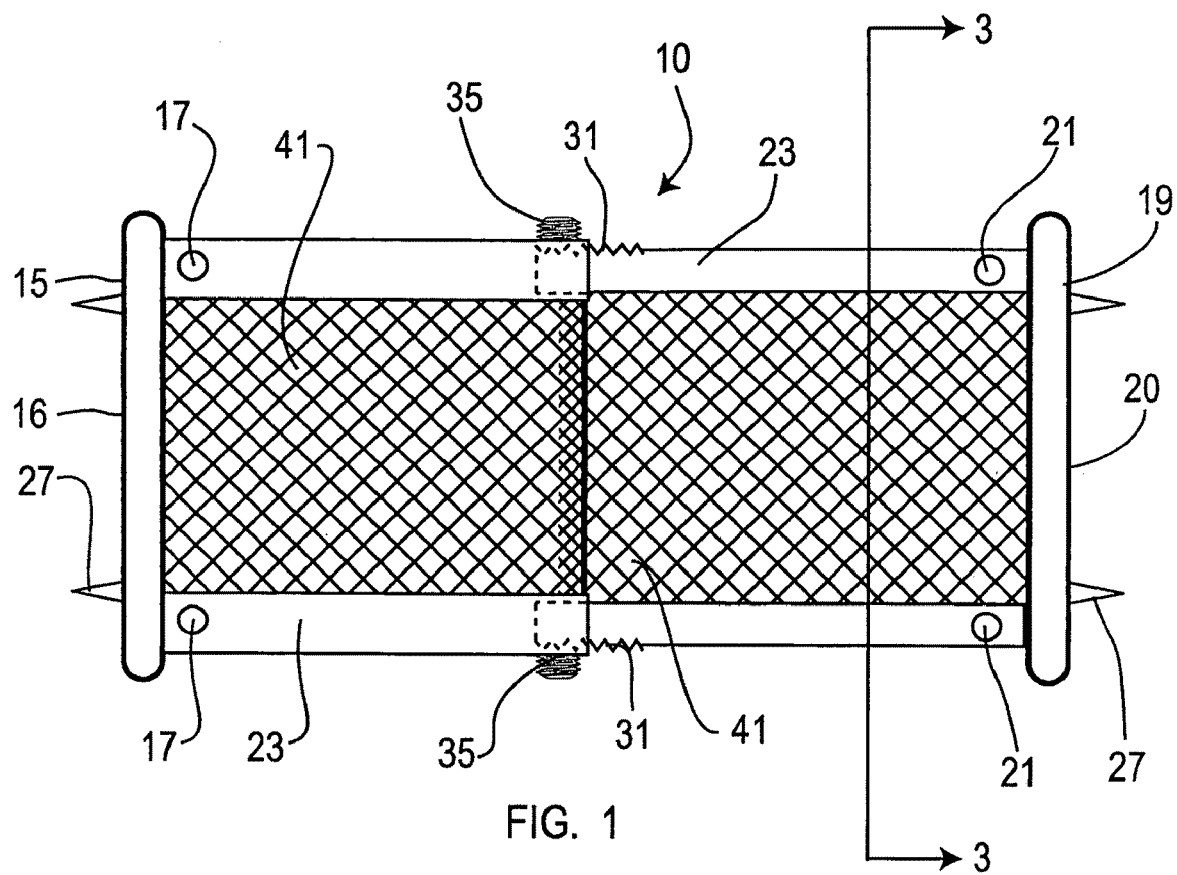
FIG. 1 shows the implant in its extended position.
Figure 2:
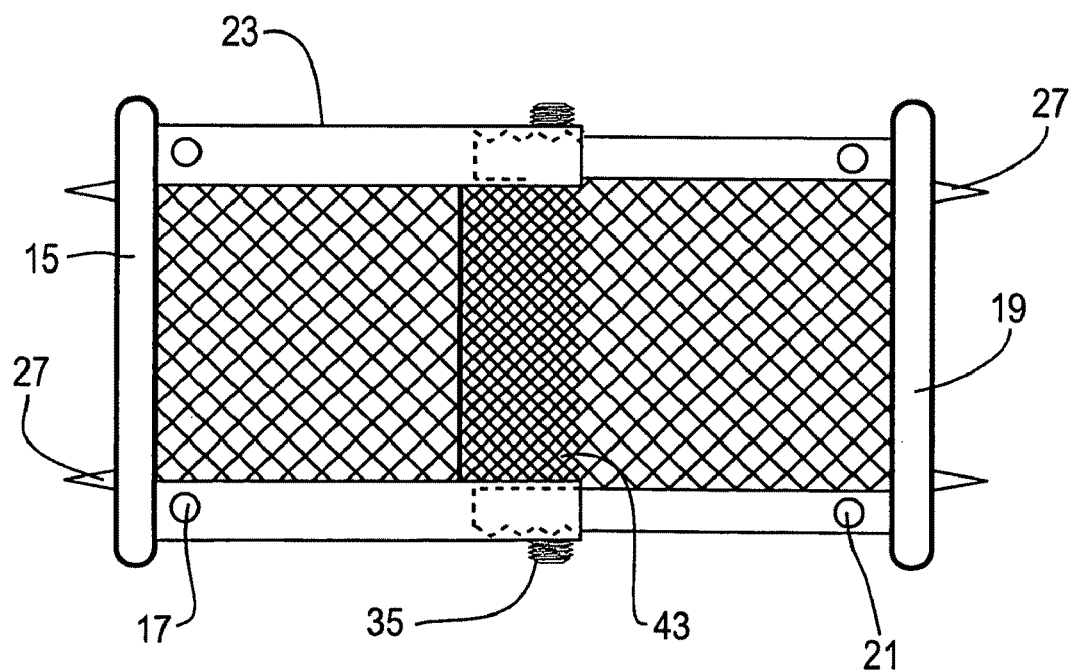
FIG. 2 shows the implant in its retracted position.
Figure 3:
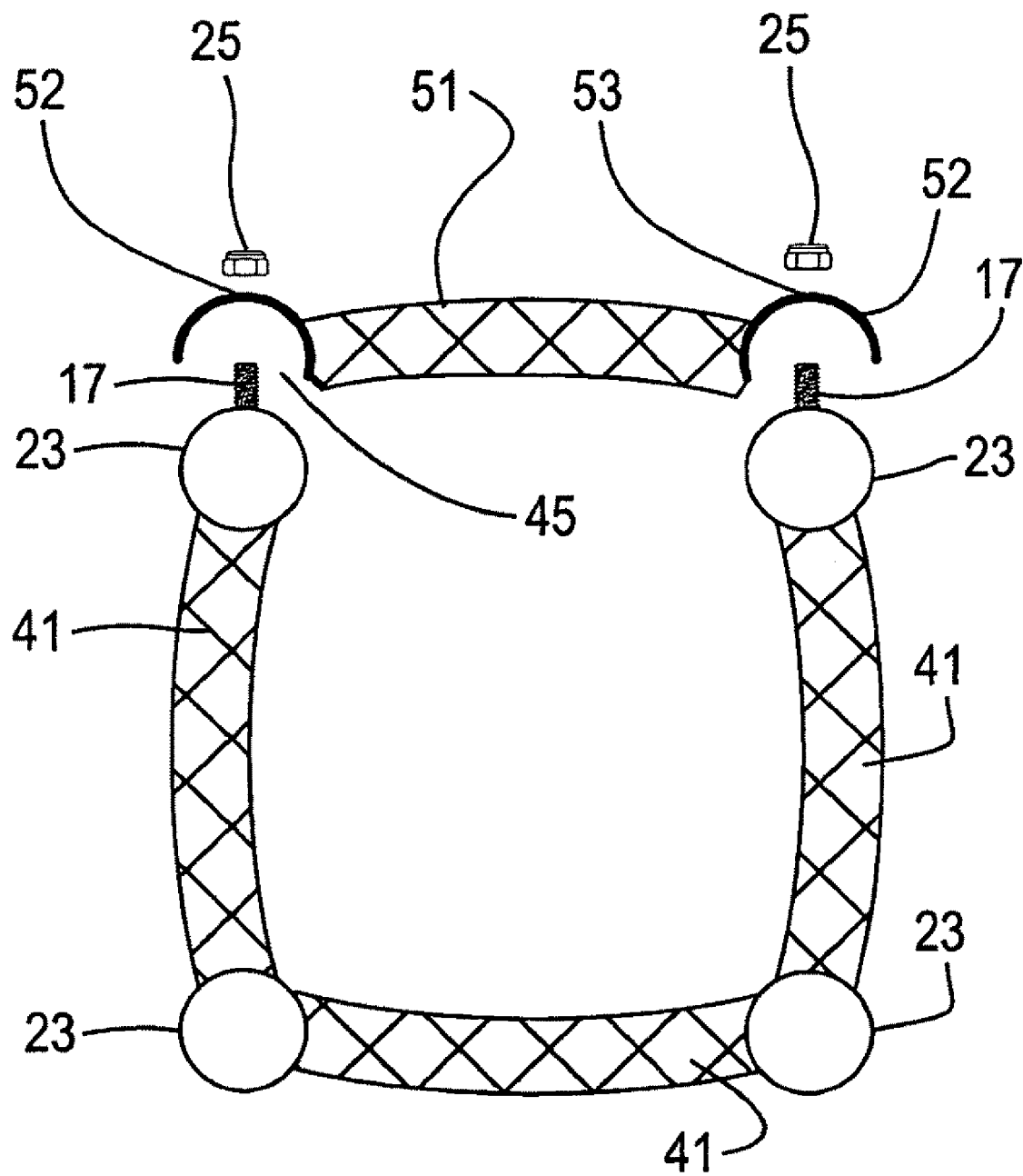
FIG. 3 is a sectional view taken through line 3-3 of FIG. 1 showing the removable cage wall.
Figure 4:
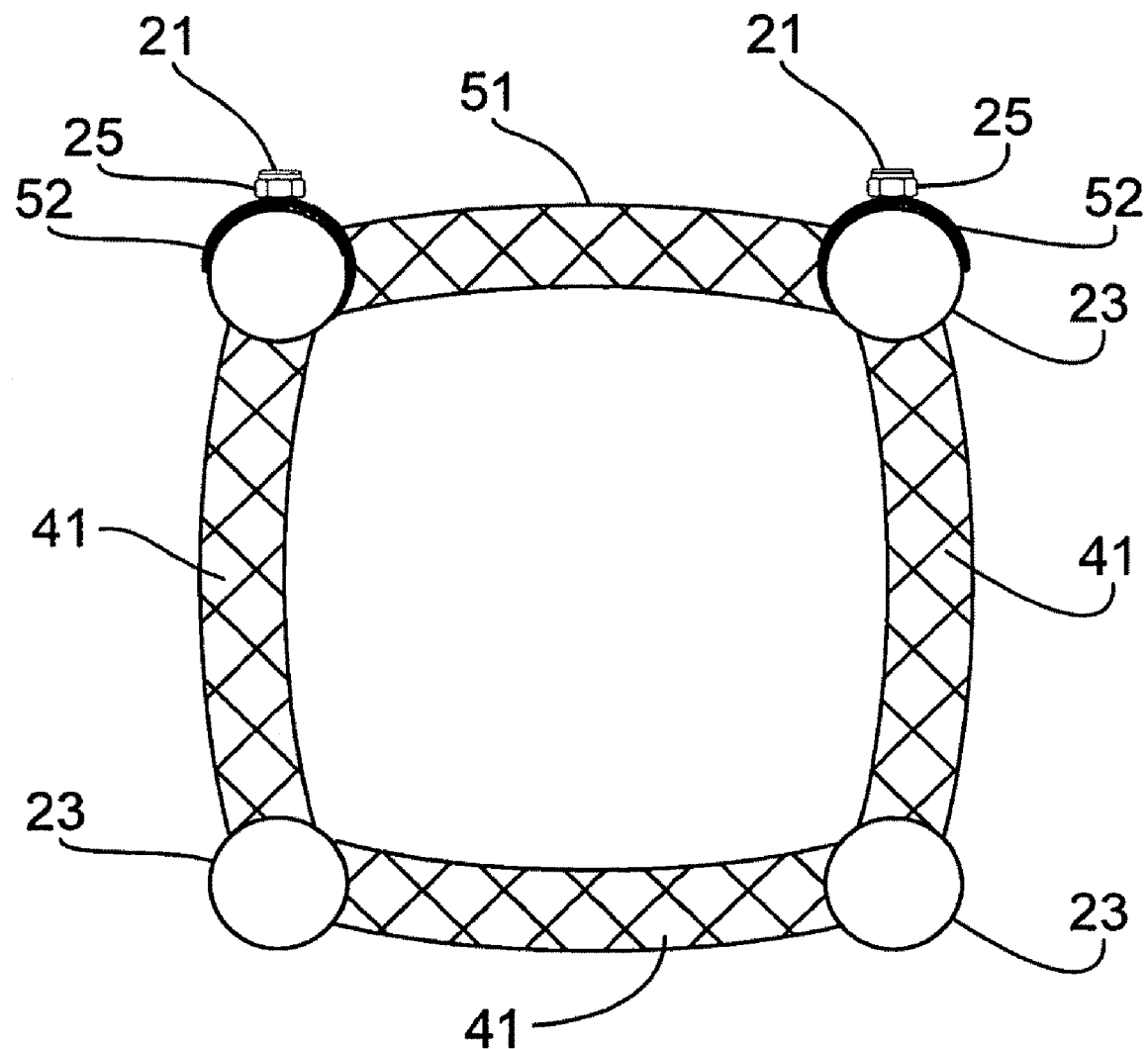
FIG. 4 is a view similar to FIG. 3 with the mesh insert in the installed position.
Figure 5:
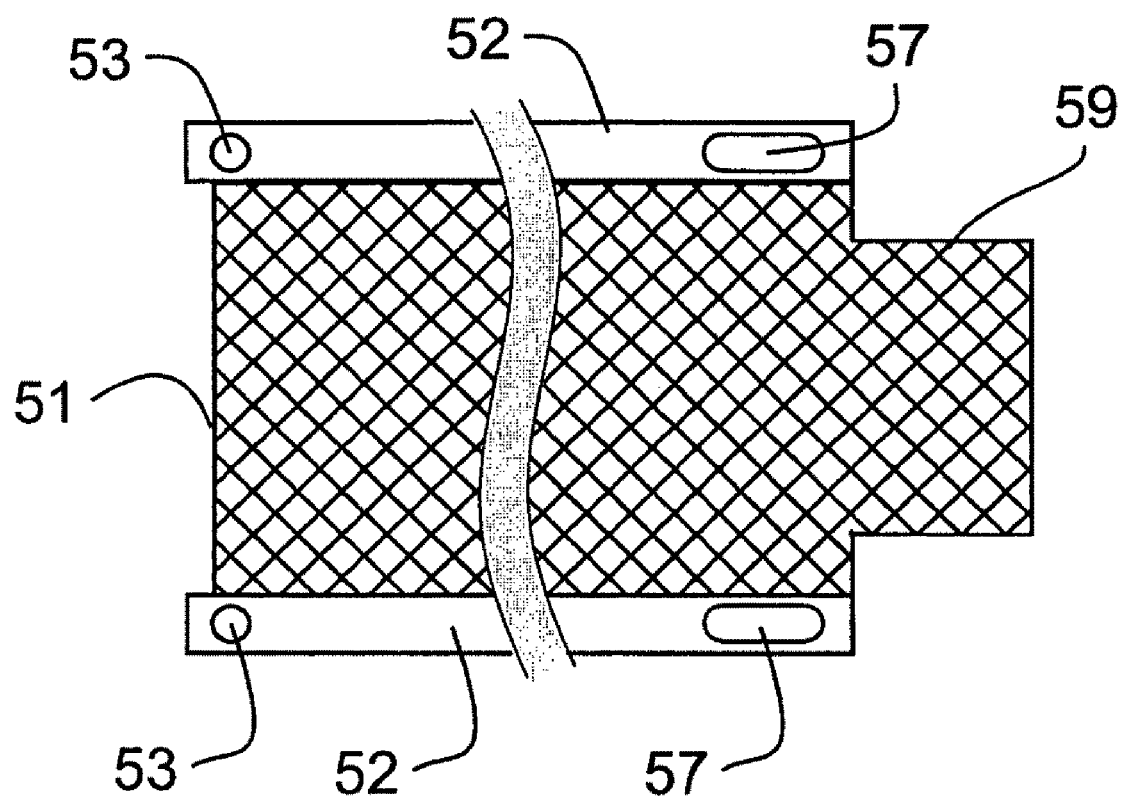
FIG. 5 is an expanded plan view of the mesh insert.
Figure 8:
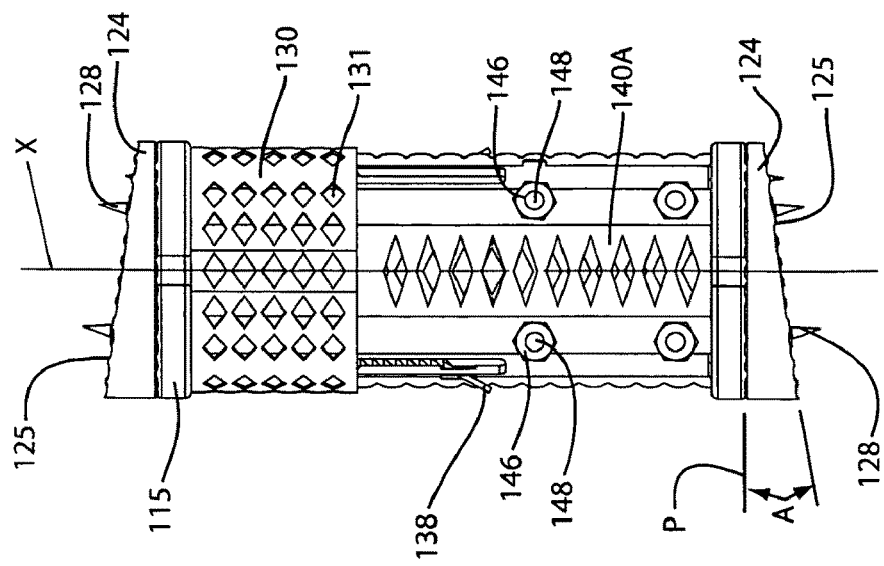
FIG. 8 is a view similar to FIG. 7 showing the implant rotated 90° about it longitude and axis.

FIGS. 1-5 show the variable height vertebral body replacement implant of the present invention. The implant 10 has a first end ring 15 and a second end ring 19. A plurality of telescopically variable length rods 23 extend between the first end ring 15 and the second end ring 19. The telescoping rods 23 maintain the first and second end rings in generally parallel, spaced apart relationship. The first and second end rings are generally ovoid or rectangular in shape and are designed to engage the end plates of adjacent vertebrae. The first end ring 15 has a first engagement side 16 and the second end ring 19 has a second engagement side 20 wherein the first and second engagement sides are disposed to engage the adjacent vertebrae. A plurality of serrations or projections 27 can be positioned on the engagement sides of the first and second end rings to assist with securing the first and second end rings in the desired position with respect to the adjacent vertebrae. The end rings 15 and 19 as well as the telescoping rods 23 are made of titanium although other materials may be used for these components.

Four telescoping rods 23 maintain the first and second end rings in spaced apart relationship. As the first and second end rings are substantially rectangular in shape a telescoping rod 23 can be positioned at generally each corner of the first and second end rings. It should be understood that other shapes can be utilized for the first and second end rings. Shapes such as ovoid, trapezoid and other generally four sided shapes can be utilized for the end rings. The telescoping rods 23 are positioned on the end rings in a manner that allows the telescoping rods 23 to provide the necessary support for the end rings. This position for the telescoping rods will maintain the first end ring 15 and second end ring 19 in an aligned spaced apart relationship. A ratchet mechanism 31 is included on at least one of the telescoping rods 23 to allow the telescoping rod to be varied in length in finite increments and to maintain the telescoping rod in the desired position whereby the first and second end ring provide the desired spacing between adjacent vertebrae in the spine. It is desirable to include a ratchet mechanism 31 on at least two of the telescoping rods 23 to assist in maintaining the desired length of the implant or cage and to keep first and second end rings in an appropriate position. If two ratchet mechanisms 31 are utilized, it is preferable to place the ratchet mechanisms on telescoping rods 23 that are in diagonally opposed relationship in the implant 10. However, it should be understood that the number of ratchet mechanisms utilized in the implant 10 can be varied as long as the proper orientation for the first end ring 15 and second end ring 19 can be achieved and maintained to provide the proper spacing between the adjacent vertebrae in the spine. The ratchet mechanism 31 has a release feature to allow the telescoping rods 23 to be adjusted until just the proper length is achieved for providing the desired spacing between the adjacent vertebrae in the spine. A set screw 35 is provided on each telescoping rod 23 and the set screw 35 is utilized to releasably lock the telescoping rod 23 in the desired position once the appropriate spacing has been achieved between the adjacent vertebrae.

The telescoping rods 23 can be straight or have a slight curvature depending on the configuration of the area of the spine that is being repaired. The objective is to have the implant generally conform with the shape of the spine in the area that is being repaired and to maintain the adjacent vertebrae in a position that is consistent with the normal location of the adjacent vertebrae in the spine before the injury. The telescoping rods 23 usually have a range of expansion up to 20 mm. If more expansion is needed, an implant with longer telescoping rods should be utilized.

An expandable mesh wall 41 is positioned to extend between the first end ring 15 and the second end ring 19. The mesh is usually made of titanium similar to the telescopic rods. The expandable mesh wall 41 defines an opening 45 for providing access to the interior of the implant 10. The mesh wall is interconnected with the four telescoping rods 23 to structurally support and assist in locating the mesh wall 41. To provide for expansion for the mesh wall, it may be desirable to secure one portion of the mesh wall to the first end ring 15 and to secure a second portion of the mesh wall 41 to the second end ring 19. The first and second portions of the mesh wall will extend to be in an overlapping relationship generally in the center of the implant 10. The overlap 43 (FIG. 2) for the first and second portions of the mesh wall is sufficient to allow for any expansion of the implant due to the extension of the telescoping rods 23. Usually, the mesh wall 41 extends substantially around three sides of the generally rectangular first and second end rings. The opening 45 defined by the mesh wall 41 is, therefore, usually one side wall that extends between the first end ring 15 and the second end ring 19.

A mesh insert 51 is releasably secured to the two telescoping rods 23 on opposite sides of the opening 45 to cover the opening 45. The mesh insert 51 is made of the same general material as the mesh wall 41. The mesh insert 51 has a channel 52 positioned on each side of the insert. The channels provide strength to the mesh insert and the channels are designed to fit over and engage the telescoping rods 23. The mesh insert 51 has two holes 53 positioned at one end of the mesh insert and two slots 57 positioned in the opposite end of the mesh insert 51. The holes 53 and slots 57 are preferably located in the channels 52 located on each side of the mesh insert. A threaded projection 17 is positioned on each of the two telescoping rods 23 on opposite sides of the opening 45 adjacent the first end ring 15 so that the threaded projections extend in a direction that is substantially perpendicular to the telescoping rods 23. A threaded projection 21 is positioned on each of the two telescoping rods 23 on opposite sides of the opening near the second end ring 19 so that the threaded projections 21 extend in a direction that is substantially perpendicular to the telescoping rods 23. The threaded projections 17 are disposed to be in alignment with and engage the holes 53 in the mesh insert 51. The threaded projections 21 on rods 23 adjacent the second end ring 19 are disposed to be in alignment with and engage the slots 57 in the opposite end of the mesh insert 51. Nuts 25 can be threadingly positioned on the threaded projections 17 and the threaded projections 21 to releasably secure the mesh insert 51 over the opening 45 in the mesh wall 41. The slots 57 in one end of the mesh insert 51 allow the mesh insert to accommodate expansion and contraction of the implant due to changes in the length of the telescoping rods 23. The lengths of the slots 57 are at least as long as the anticipated range of movement for the telescoping rods 23 and preferably are a little bit longer than the range of motion for the telescoping rods 23. The end of the mesh insert 51 that contains the slots 57 has section 59 that extends into the second end ring 19 a distance that is also sufficient to accommodate the range of motion for the telescoping rods 23. In this manner the mesh insert will be able to accommodate the expansion and contraction anticipated for the implant 10. It is also anticipated that slots could be positioned on each end of the mesh insert 51 to allow the mesh insert to accommodate variations in length of the implant 10 on either end of the mesh insert.

If desired, the mesh insert 51 could be connected to the first and second end rings 15 and 19 rather than to the telescoping rods 23.

In operation the implant 10 is positioned in the body of a patient to provide the desired spacing when one or more vertebrae have been removed from the spine of the patient. The first end ring 15 and the second end ring 19 are positioned in a not completely extended orientation to allow the implant 10 to be more readily inserted into the proper location in the spine of the patient. Once the implant 10 is positioned between the adjacent vertebrae, the telescoping rods 23 can be advanced to engage the adjacent vertebrae and to position the adjacent vertebrae in the desired spatial relationship. The ratchet mechanism 31 is utilized to advance the telescoping rods 23 in small increments until the desired spacing between the adjacent vertebrae is achieved. Once the desired positioned for the first ring 15 and second ring 19 has been achieved, the set screws 35 on each telescoping rod 23 can be engaged to lock the telescoping rods in the desired position. Bone or bone graft material can then be positioned in the implant 10 through the opening 45 in the mesh wall 41. The bone or bone graft material normally completely fills the interior of the implant 10. Once the appropriate amount of bone or bone graft material is positioned in the implant 10, the mesh insert 51 is positioned on the threaded projections 17 and 21 and secured in position with nuts 25 to close the opening 45 in the mesh wall 41. The mesh insert 51 presses against the bone or bone graft material and acts to compact the bone or bone graft material in the interior of the implant 10. Compaction of the bone or bone graft material assist in the fusing of the bone or bone graft material with the adjacent vertebrae to complete the surgical repair of the spine.

Figure 6:
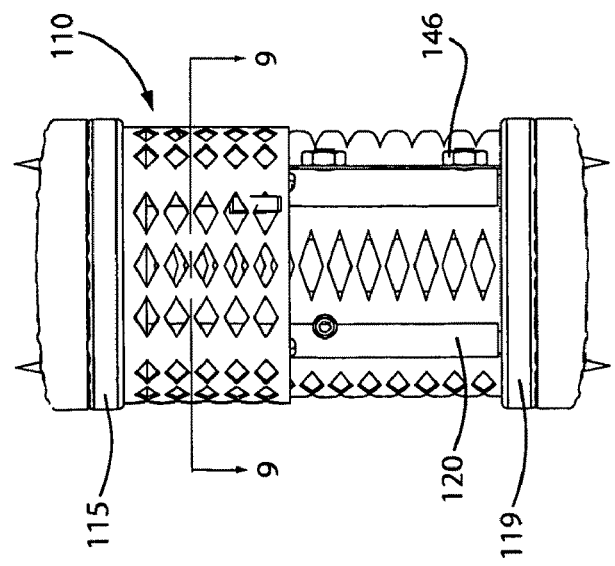
FIG. 6 is an elevational view of a modified implant in its retracted position.
Figure 10:
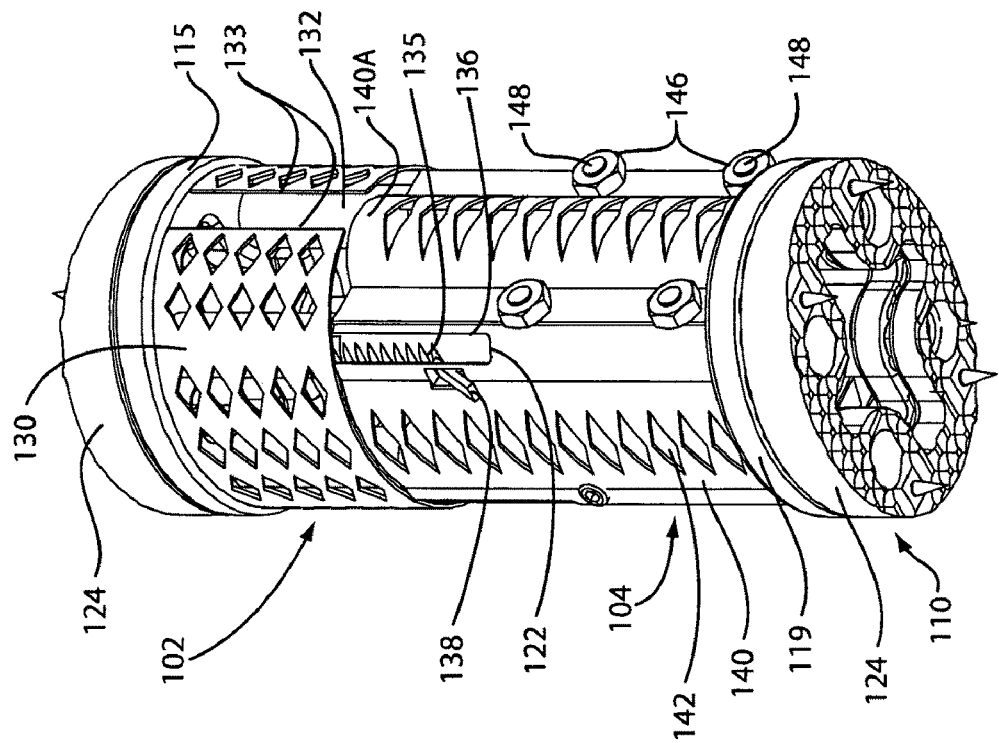
FIG. 10 is a perspective view of the implant as viewed from the lower end of FIG. 7.
Figure 9:
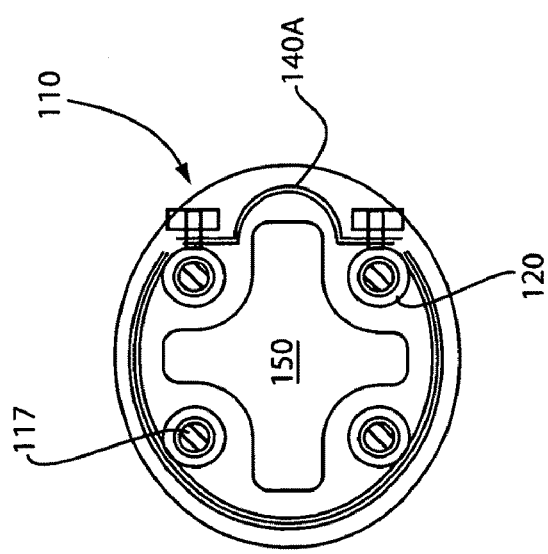
FIG. 9 is a sectional view taken through line 9-9 of FIG. 6.
Figure 11:
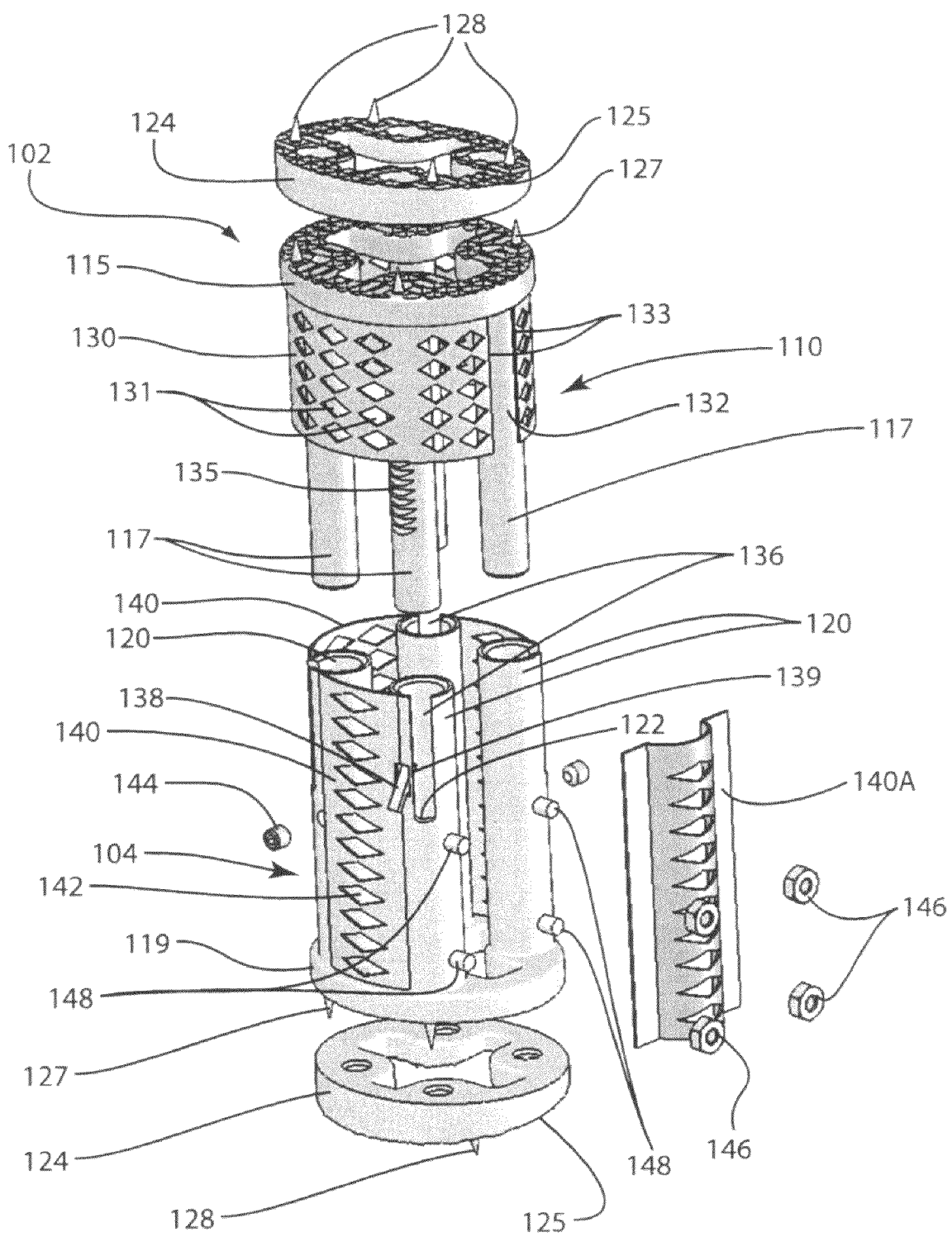
FIG. 11 is an exploded view of the modified implant.
Figure 12:
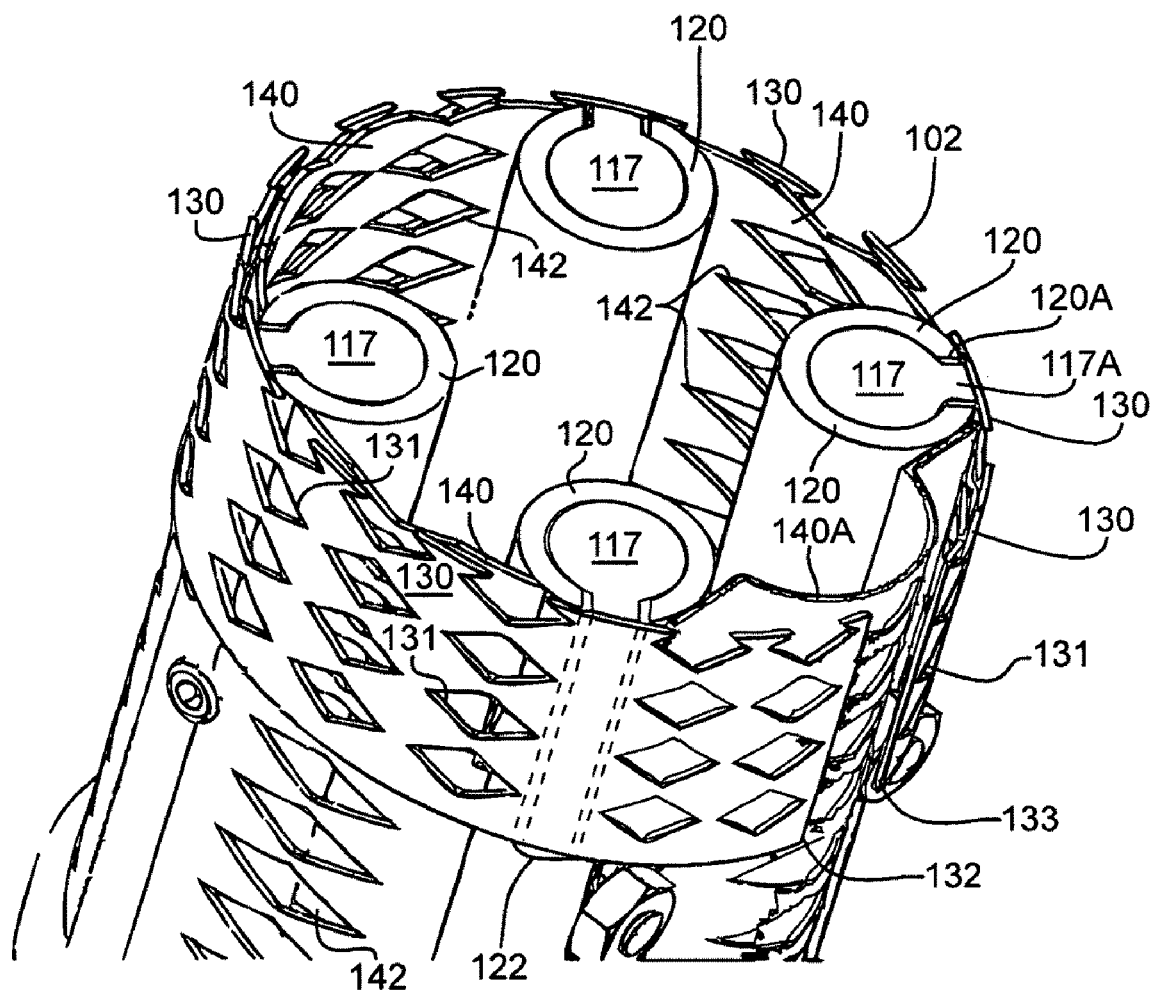
FIG. 12 is a fragmentary perspective view taken through line 9-9 of FIG. 6.

Referring now to FIGS. 6-11, there is shown a modified implant which will hereinafter be referred to as expandable corpectomy cage 110. The corpectomy cage 110 includes two slidably engageable assembly members, namely, a first assembly member 102 having a first end ring 115 and a second assembly member 104 having a second end ring 119. As best seen in FIGS. 11 and 12, extending from the first end ring 115 are four insertion rod sections 117 spaced apart from one another and extending parallel to one another and to an axis X (see FIG. 8) centered between said insertion rod sections 117. Each of the insertion rod sections 117 has an outwardly extending rib 117A extending axially from a point near the first end ring 115 to a point approximately midway of their respective lengths. Extending from the second end ring 119 are four hollow cylindrical members 120 which, when the second end ring 119 is properly aligned with the first end ring 115, will result in the hollow members 120 extending from end ring 119 being axially aligned with the insertion members 117 extending from the first end ring 115. The hollow members 120 are sized to receive therein the respective insertion sections 117 extending from the first end ring 115. The hollow members 120 are each provided with a slot 136 extending from their distal ends opposite the second end ring to a slot end 122. The slot 136 is sized breadthwise and lengthwise to completely receive therein the outwardly extending rib 117A when the corpectomy cage is at its shortest length as shown in FIG. 6.

The first end ring 115 and the second end ring 119 may have a circular, oval or other cross sectional shape depending on the anatomy of the patient. Similarly, the insertion rod sections 117 and the hollow members 120 may be arranged such that an arcuate line drawn through their respective axes may define a similar circular, oval or other shape although somewhat smaller.

As was the case with the embodiment of FIGS. 1-5, each of the first end ring 115 and second end ring 119 has extending therefrom a plurality of serrations or projections 127 to assist in securing the first and second end rings 115, 119 in the desired position with respect to the adjacent vertebrae of the patient.

Depending upon the anatomy of the patient, it may be desirable to also provide a wedge-shaped end cap 124 on one or both of the end rings 115, 119. The respective end caps 124 each has a distal end surface 125 disposed at an angle A (see FIG. 8) in the range of 2° to 10° with respect to a plane P perpendicular to the axis X centered between the joined insertion rod sections 117 and hollow members 120. The end caps 124 can be fastened to the respective end rings 115, 119 by any desired fastening means. Each of the end caps 124 has a plurality of serrations or projections 128 extending from its distal end surface 125.

Substantially encircling the insertion rod sections 117 extending from the first end ring 115 is a perforated sleeve 130 which extends axially from the first end ring 115 toward the second end ring 119 overlying approximately one-half the length of the respective insertion rod sections. The perforated sleeve 130 has a plurality of perforations 131 which, preferably, are aligned in rows parallel the axis X and aligned in rows extending therearound in a plane perpendicular to the axis X. The perforated sleeve 130 extends around the axis to define an arc on the order of 350° to 355° such that there is a gap 132 between the opposing ends 133 of the perforated sleeve 130. As can be seen most clearly in FIG. 12, the ribs 117A extend outwardly beyond the outer surface 120A of the hollow members 120 and are welded or otherwise joined to the inner surface of the perforated sleeve 130.

At least one and preferably more of the insertion rod sections 117 includes a series of teeth 135 forming part of a ratchet mechanism to assist in maintaining the desired length of the corpectomy cage 110. As previously mentioned, the hollow members 120 extending from the second end ring 119 are provided with axially extending slots 136 extending from their receiving ends approximately half the distance toward the second end ring 119. Positioned adjacent the slots 136 in an area spaced from the receiving end of the hollow sections 120 is an engagement member 138 of the ratchet mechanism, which engagement member 138 includes an inwardly extending projection 139 for engaging the teeth 135 of the aligned insertion rod section 117 extending from the first end ring 115.

Positioned between adjacent ones of the respective hollow members 120 and extending from the second end ring 119 toward the first end ring 115 are a plurality of arcuate sections 140, each of which has a series of spaced apart perforations 142 aligned in rows extending axially from a position adjacent the second end ring 119 to the opposing end of each arcuate section and aligned in rows perpendicular to the axis X. Each arcuate section 140 may be affixed to one or both of the adjacent hollow members 120 by a fastening member 144 such as a screw and/or screw and nut arrangement by welding or by other fastening means. Three of the arcuate sections 140 are attached to the second end ring 119 and to the respective hollow members 120 extending therefrom. As may be seen most clearly in FIGS. 8, 11 and 12, the fourth arcuate section 140A is separate from the rest of the corpectomy cage 110 as delivered to the operating room. The arcuate section 140A is similar in size to the other arcuate sections 140 and may be attached to the adjacent hollow members 120 by means of nuts 146 engaged to threaded studs 148 secured to and extending outwardly from two adjacent hollow members 120 as seen most clearly in FIGS. 8 and 11.

As maybe seen from FIG. 11, the first assembly member 102 maybe joined to the second assembly member 104 by aligning the four insertion rod sections 117 with the respective hollow members 110 and moving the first assembly member 102 toward the second assembly member 104 to slide the insertion rod sections 117 into the respective aligned hollow members 120. When the insertion sections 117 are inserted to their maximum extent, the corpectomy cage 110 will be at its shortest length as shown in FIG. 6. When the first assembly member 102 is positioned relative to the second assembly member 104 as shown in FIG. 6, the perforated sleeve 130 of such first assembly member 102 will encircle the hollow sections 120 and the arcuate sections 140 and 140A secured thereto.

Figure 7:
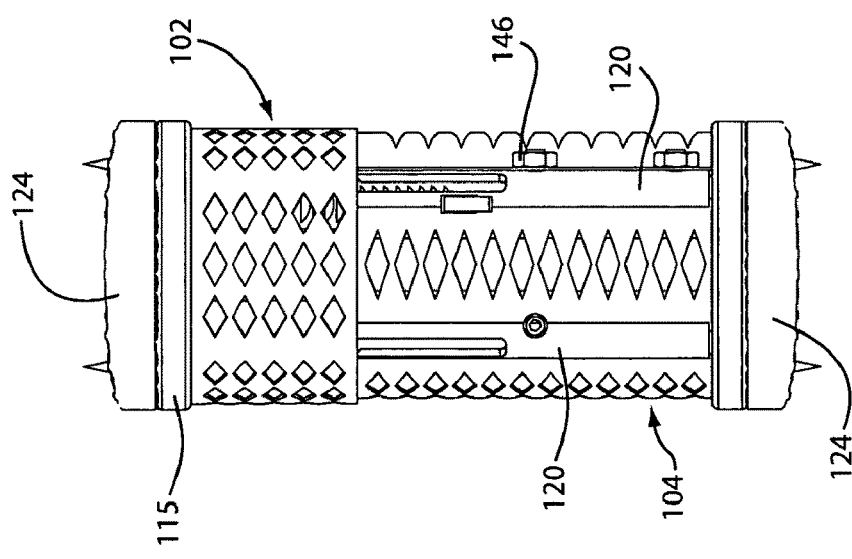
FIG. 7 is a view similar to FIG. 6 showing the implant in its extended position.

In order to have the insertion sections 117 moved into the hollow sections 120 to the maximum extension as shown in FIG. 6, it will be necessary to pivot the engagement member 138 to retract the projection 139 to a position to avoid engaging the teeth 135 of the insertion rod sections 117 during that time. When the first assembly member 102 is moved away from the second end ring 119, and moved to the desired extended position suitable to the anatomy of the patient, the engagement member 138, which is preferably spring loaded, will move to a position at which the projection 139 engages the teeth 135 of the insertion sections 117 to retain the corpectomy cage 110 in its expanded position as shown in FIG. 7. With corpectomy cage 110 locked in such expanded position, bone chips, bone splints and/or other bone graphs or fusion of materials may be positioned in the cavity 150 (see FIG. 9) defined by the assembled structure following which, the removable fourth arcuate section 140A maybe engaged to the studs 148 of the hollow members 120 and affixed thereto by the threaded nuts 146.

Figure 13:
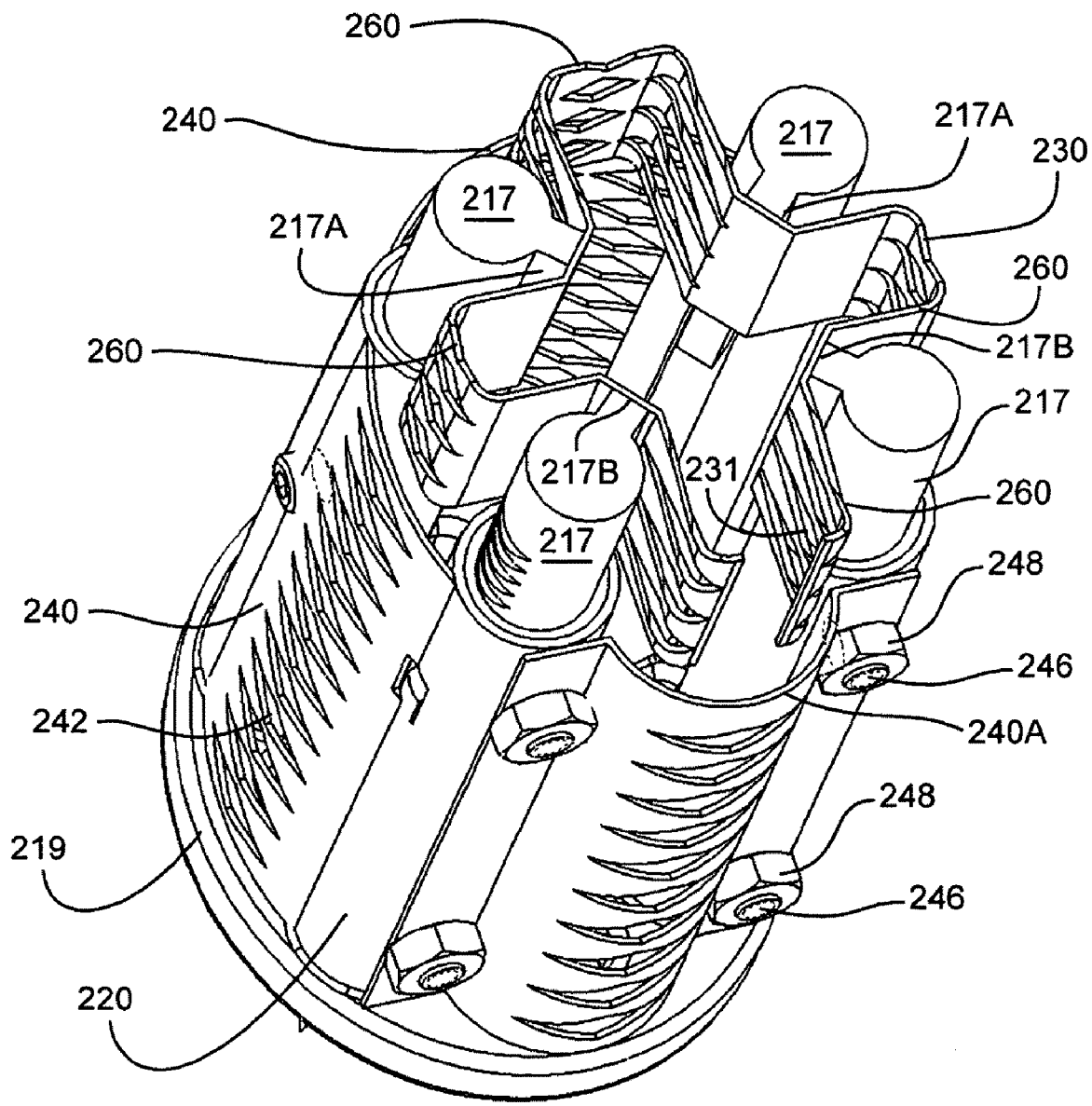
FIG. 13 is a perspective view of a portion of further modification.
Figure 14:
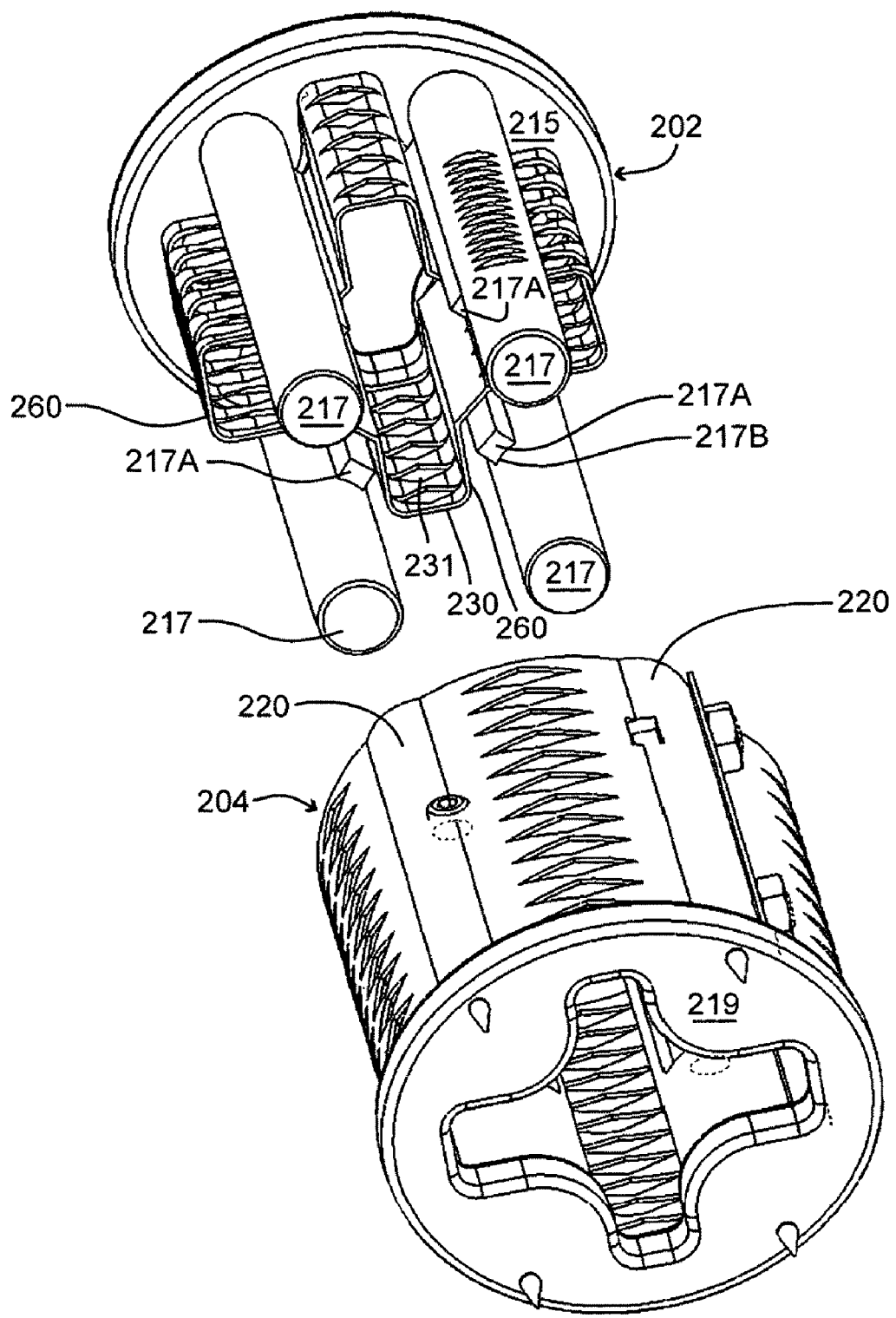
FIG. 14 is an exploded view, in perspective, of the further modification of FIG. 13.
Figure 15:
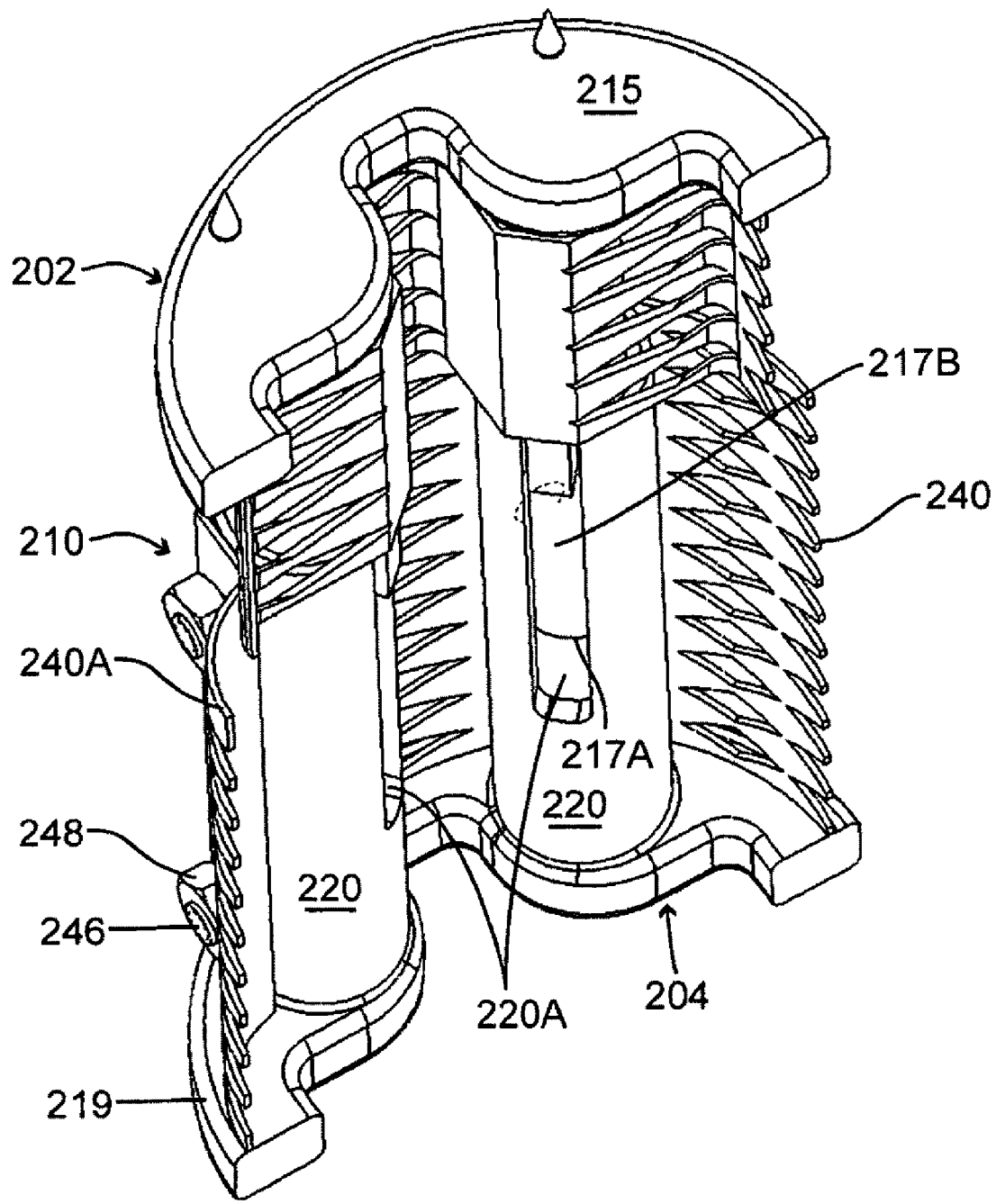
FIG. 15 is a sectional view taken through the longitudinal axis of the assembled further modification.

Referring to FIGS. 13-15, there is shown a further modification of the corpectomy cage 210, a section of which is shown in FIG. 15 in which the first assembly member 202 is joined to the second assembly member 204 to form the assembled further modified corpectomy cage 210. The major difference between the embodiment of FIGS. 13-15 is that the insertion rod sections 217 have ribs 217A which, extend inwardly toward the longitudinal axis of the assembled cage 210 rather than the outwardly extending ribs 117A of the embodiment of FIGS. 6-12.

Thus, the corpectomy cage 210 first assembly member 202 has four insertion rod sections 217 extending from a first end ring 215. Welded or otherwise secured to the innermost surface 217B of the inwardly extending ribs 217 is a perforated sleeve 230 having a series of perforations 231. The perforated sleeve 230 defines a closed loop which maybe defined as having four legs 260, with each leg 260 extending away from the longitudinal axis and positioned between adjacent ones of the insertion rod sections 217. (See FIGS. 13 and 14).

The second assembly member 204 has four hollow cylindrical members 220 extending upwardly from a second end ring 219. Each hollow member 220 has a slot 220A facing inwardly toward the longitudinal axis and sized to receive therein the rib 217A of the insertion rod sections 217.

Secured between adjacent ones of the hollow members 220 are three arcuate sections 240 each of which is provided with a series of perforations 242. A fourth arcuate section 240A, which is removable, maybe attached between adjacent hollow sections 220 by means of studs 246 and threaded nuts 248.

As maybe clearly seen from FIGS. 13-15, under this embodiment, the arcuate sections 240 and 240A encircle the perforated member 260 attached to the inner surfaces 217B of the ribs 217A. This is in contrast to the embodiment of FIGS. 6-12 in which the perforated sleeve 130 attached to the outer surfaces of the ribs 117A of the insertion member 117 encircled the arcuate members 140 attached to adjacent hollow members 120.

The above detailed description of the present invention is given for explanatory purposes. It will be apparent to those skilled in the art that numerous changes and modifications other than those cited can be made without departing from the scope of the invention. For example, the first assembly 102, 202 could be provided with hollow cylindrical members rather than the insertion rod sections 117 in which case, the second assembly 104, 204 would be provided with insertion rod sections 117, 217 rather than the hollow member 120, 220 as shown. Additionally, the first assembly 102, 202 and the second assembly could each have two insertion rod sections and two hollow members. Accordingly, the whole of the foregoing description is to be construed in an illustrative and not a limitative sense, the scope of the invention being defined solely by the appended claims.

I claim:

1. A variable height vertebral implant comprising:
    a first end ring and a second end ring positioned in spaced apart relationship, the first and second end rings being disposed to engage adjacent spaced apart vertebrae;
    a plurality of telescopically variable length rods extending between the first and second end rings, the plurality of rods being adjustable in length to provide the desired spacing between the first and second rings to engage the adjacent spaced apart vertebrae, at least one of the telescopically variable length rods including a ratchet mechanism for releasably securing the at least one telescopically variable length rod in a fixed position;
    an expandable mesh wall extending between the first and second rings, the mesh wall defining an opening between adjacent ones of said variable length rods for providing access to the interior of the vertebral implant; and
    a mesh insert that is releasably secured to each of said adjacent ones of said variable length rods or the first and second rings whereby the mesh insert covers the opening in the mesh wall between said adjacent ones of said variable length rods.

2. The implant of claim 1 wherein bone material is positioned through the opening in the mesh wall into an interior chamber defined by the wall of the implant whereby the bone material extends between the spaced apart adjacent vertebrae.

3. The implant of claim 2 wherein the mesh insert is secured to the variable length rods or the first and second rings after the bone material is positioned in the interior chamber of the implant, the mesh insert being disposed to engage the bone material and to compact the bone material.

4. The implant of claim 1 further including projections extending from said first and second rings for engagement with said spaced apart vertebrae.

5. A variable height vertebral implant comprising:
    a first end ring and a second end ring positioned in spaced apart relationship, the first and second end rings being disposed to engage adjacent spaced apart vertebrae;
    a plurality of telescopically variable length rods extending between the first and second end rings, the plurality of rods being adjustable in length to provide the desired spacing between the first and second rings to engage the adjacent spaced apart vertebrae, at least one of the telescopically variable length rods including a ratchet mechanism for releasably securing the at least one telescopically variable length rod in a fixed position;
    an expandable mesh wall extending between the first and second rings, the mesh wall defining an opening for providing access to the interior of the vertebral implant; and
    a mesh insert that is releasably secured to the variable length rods or the first and second rings whereby the mesh insert covers the opening in the mesh wall,
    said mesh insert being releasably secured to the variable length rods by means comprising (a) projections extending outwardly from said rods and (b) openings in said mesh insert positioned to receive said projections, at least two of said openings defining elongated slots to accommodate movement of said variable length rods.

6. A corpectomy cage for use in spine surgery comprising:
    a first assembly having a first end member, a plurality of spaced apart elongated hollow members or insertion rod sections extending from said first end member, a sleeve joined to said spaced apart hollow members or insertion rod sections; and
    a second assembly having a second end member, a plurality of spaced apart elongated hollow members or insertion rod sections extending from said second end member, each of said second end member hollow members and insertion rod sections being engageable with one of said first end member insertion rod sections or hollow members, longitudinally extending perforated members connected to adjacent ones of said second end member hollow members or insertion rod sections, one of said longitudinally extending perforated members being attachable to adjacent ones of said second end member hollow members or insertion rod sections following engagement of said first assembly to said second assembly and means to retain said first assembly in one of a plurality of fixed positions relative to said second assembly.

7. The corpectomy cage according to claim 6 wherein said means to retain comprises:
    a plurality of teeth on one or more of said insertion rod sections and a latch on one or more of said hollow members engageable with said teeth.

8. The corpectomy cage according to claim 7 wherein a slot is provided in hollow members and further including a latch adjacent said slot, said latch being engageable with said teeth.

9. The corpectomy cage according to claim 6 further including a wedge shaped end cap attached to one or both first and second end rings, said end cap having a first surface in contact with said first or second end ring and a tapered surface disposed at an angle in the range of 2° to 10° relative to a plane defined by said first surface.

10. The corpectomy cage according to claim 6 wherein said sleeve substantially encircles said spaced apart hollow members or insertion rod members and partially overlies said longitudinally extending perforated members when said first assembly is engaged to said second assembly.

11. The corpectomy cage accordingly to claim 6 wherein said perforated members, in cross section perpendicular to the longitudinal axis of said first assembly, define an arcuate path.

12. The corpectomy cage according to claim 6 wherein said first and second end members, in cross section perpendicular to the longitudinal axis of said assembled corpectomy cage, defines a circle or an oval.

13. The corpectomy cage according to claim 6 wherein one or more insertion rod sections has a rib extending radially outwardly and extending longitudinally substantially parallel to the longitudinal axis of said rod sections and at least one said elongated hollow member has a slot sized and positioned to receive said rib upon insertion of said rod sections into said hollow members.

14. The corpectomy cage according to claim 6 wherein one or more insertion rod sections has a rib extending radially from the surface of said rod section in a direction toward the longitudinal axis of said corpectomy cage and extending longitudinally substantially parallel to the longitudinal axis of said rod sections and said elongated hollow members have a slot sized and positioned to receive said rib upon insertion of said rod sections into said hollow members.

15. A corpectomy cage for use in spine surgery comprising:
a first assembly having a first end member, a plurality of spaced apart elongated hollow members or insertion rod sections extending from said first end member, each said hollow member or insertion rod section having a longitudinal axis parallel to each of the other of said longitudinal axes and cooperating to define a central axis parallel to each of said longitudinal axes and a sleeve connected to said spaced apart hollow members or rod sections; and
a second assembly having a second end member, a plurality of spaced apart elongated hollow members or insertion rod sections extending from said second end member, each of said second end member hollow members and insertion rod sections being engageable with one of said first end member insertion rod sections or hollow members, longitudinal perforated members extending substantially parallel to said central axis connected to adjacent ones of said second end member hollow members or insertion rod sections, one of said longitudinal perforated members being attachable to adjacent ones of said second end member hollow members or insertion rod sections following engagement of said first assembly to said second assembly and means to retain said first assembly in one of a plurality of fixed positions relative to said second assembly.

16. The corpectomy cage accordingly to claim 15 wherein said perforated members, in cross section perpendicular said central axis, define an arcuate path.

17. The corpectomy cage according to claim 15 wherein one or more of said insertion rod sections has a rib extending outwardly in a direction away from said central axis and longitudinally in a direction parallel to said central axis and said hollow member have a slot sized and positioned to receive said rib upon insertion of said rod sections into said hollow members.

18. The corpectomy cage according to claim 17 wherein said sleeve at least partially encircles the group of hollow members and insertion rod sections extending from said first end member.

19. The corpectomy cage according to claim 18 wherein said sleeve at least partially encircles the group of hollow members and insertion rod sections extending from said second end member and at least some of said longitudinal perforated members upon engagement of said first assembly to said second assembly.

20. The corpectomy cage according to claim 15 wherein one or more of said insertion rod sections has a rib extending inwardly in a direction toward said central axis and longitudinally in a direction parallel to said central axis and said hollow members have a slot sized and positioned to receive said rib upon insertion of said rod sections into said hollow member.

21. The corpectomy cage accordingly to claim 20 wherein said sleeve is attached to said inwardly extending rib.

22. The corpectomy cage according to claim 15 wherein said means to retain comprises:
a plurality of teeth on one or more of said insertion rod sections and a latch on one or more of said hollow members engageable with said teeth.

23. The corpectomy cage according to claim 15 further including a wedge shaped end cap attached to one or both first and second end rings, said end cap having a first surface in contact with said first or second end ring and a tapered surface disposed at an angle in the range of 2° to 10° relative to a plane defined by said first surface.

24. The corpectomy cage according to claim 15 wherein at least one of said first and second end members, in cross section perpendicular to the longitudinal axis of said assembled corpectomy cage, defines a circle or an oval.

* * * * *